US011028082B2

(12) United States Patent
Bertolini et al.

(10) Patent No.: US 11,028,082 B2
(45) Date of Patent: Jun. 8, 2021

(54) PROCESS FOR THE PREPARATION OF A NOVEL UMECLIDINIUM SYNTHESIS INTERMEDIATE

(71) Applicant: OLON S.P.A., Rodano MI (IT)

(72) Inventors: Giorgio Bertolini, Rodano MI (IT); Corrado Colli, Rodano MI (IT); Filippo Nisic, Rodano MI (IT); Mara Sada, Rodano MI (IT); Stefania Bertuolo, Milano MI (IT); Silvano Ronzoni, Milano MI (IT); Stefano Maiorana, Milano MI (IT); Romano Di Fabio, Milano MI (IT)

(73) Assignee: OLON S.P.A., Rodano MI (IT)

( * ) Notice: Subject to any disclaimer, the term of this patent is extended or adjusted under 35 U.S.C. 154(b) by 0 days.

(21) Appl. No.: 16/617,928

(22) PCT Filed: May 28, 2018

(86) PCT No.: PCT/IB2018/053767

§ 371 (c)(1),
(2) Date: Nov. 27, 2019

(87) PCT Pub. No.: WO2018/220501

PCT Pub. Date: Dec. 6, 2018

(65) Prior Publication Data

US 2020/0102300 A1 Apr. 2, 2020

(30) Foreign Application Priority Data

May 30, 2017 (IT) ........................ 102017000058796

(51) Int. Cl.
*C07D 453/02* (2006.01)

(52) U.S. Cl.
CPC .................................. *C07D 453/02* (2013.01)

(58) Field of Classification Search
CPC .................................................... C07D 453/02
See application file for complete search history.

(56) References Cited

FOREIGN PATENT DOCUMENTS

| | | | |
|---|---|---|---|
| CN | 105461710 | 4/2016 | |
| CN | 108 069 956 | 5/2018 | |
| WO | 2005/104745 | 11/2005 | |
| WO | 2014/027045 | 2/2014 | |
| WO | WO-2014027045 A1 * | 2/2014 | ............. A61P 11/00 |

OTHER PUBLICATIONS

Gu, J., "Convenient new synthesis of umeclidinium bromide." Synthetic Communications 48.9 (2018): 995-1000.*

European Search report dated Jan. 15, 2018 by the EPO for Italian priority application No. 102017000058796.

International search report and written opinion issued by the EPO dated Oct. 23, 2018 for International patent application No. PCT/IB2018/053767.

International Preliminary Report on Patentability issued by the EPO dated Dec. 3, 2019 for International patent application No. PCT/IB2018/053767.

Dramane I Lainei et al: "Discovery of Novel 1-Azoniabicyclo[2.2.2]octane Muscarinic Acetylcholine Receptor Antagonists", Journal of Medicinal Chemistry, American Chemical Society, vol. 58, No. 8, Apr. 23, 2009 (Apr. 21, 2009), pp. 2493-2505, XP002691510.

Jianhui Gu et al: "Convenient new synthesis of umeclidinium bromide", Synthetic Communications, voi. 48, No. 9, May 3, 2018 (May 3, 2018), pp. 995-1000, XP055754295, ISSN: 0039-7911, 001: 10.1080/00397911.2017.1348525.

Office Action issued by the EPO dated Dec. 2, 2020 for corresponding European application No. 18731525.4.

* cited by examiner

*Primary Examiner* — John M Mauro
(74) *Attorney, Agent, or Firm* — Silvia Salvadori

(57) ABSTRACT

The present invention relates to a process for the preparation of a novel and versatile synthesis intermediate and its use in the preparation of umeclidinium. The invention also relates to some reference standards allowing to detect impurity traces recurring in the preparation of umeclidinium and a process for their preparation.

14 Claims, 2 Drawing Sheets

PROCESS FOR THE PREPARATION OF A NOVEL UMECLIDINIUM SYNTHESIS INTERMEDIATE

This application is a U.S. national stage of PCT/IB2018/053767 filed on 28 May 2018, which claims priority to and the benefit of Italian Application No. 102017000058796 filed on 30 May 2017, the contents of which are incorporated herein by reference in their entireties.

SUMMARY OF THE INVENTION

The present invention relates to a process for the preparation of a novel and versatile synthesis intermediate and its use in the preparation of umeclidinium. The invention also relates to some reference standards allowing to detect impurity traces recurring in the preparation of umeclidinium and a process for their preparation.

TECHNICAL FIELD

Umeclidinium, in particular umeclidinium bromide, is a compound used in the therapy of subjects affected by chronic obstructive pulmonary disease.

WO2005/104745 and WO2014/027045 describe a process for the preparation of a key intermediate in the synthesis of umeclidinium, providing the following reaction:

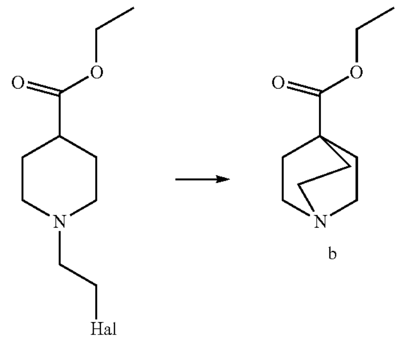

a b wherein Hal is a halogen atom and the subsequent treatment of compound (b) with phenyllithium in excess to the compound of formula (b).

The cyclization, to give the quinuclidine ring, is generally carried out in the presence of bis(trimethylsilyl)amides of alkaline metals, for example lithium, or diisopropylamide of alkaline metals. These bases, in addition to being very expensive, are highly unstable and must be prepared in situ or, alternatively, purchased as very diluted solutions in organic solvents.

Furthermore, the subsequent reaction bringing to the simultaneous introduction of the two phenyls, that is conventionally carried out with phenyllithium, uses two or more phenyllithium equivalents, as it is evident. The Applicant further found that impurities of the biphenyllithium type are present in the commercial phenyllithium and generate corresponding impurities in the reaction product and that such impurities, being similar to the desired compound, are very difficult to eliminate.

All of the above mentioned factors are drawbacks reducing yields, increasing costs and industrial resources needed for producing such synthesis intermediates of umeclidinium. Therefore a need exists to provide an alternative process for the preparation of the umeclidinium intermediates, that obviates the drawbacks of the known art.

OBJECTS OF THE INVENTION

A purpose of the invention is to provide novel and versatile synthesis intermediates in highly purified form, and a process for their preparation.

A further purpose of the invention is to provide the use of such intermediates in the preparation of umeclidinium.

A further purpose of the invention is to provide a process for the preparation of umeclidinium, giving good yields and purity and being industrially convenient.

A further purpose of the invention is to provide a very versatile novel intermediate compound, that can be functionalized in different ways to give, on one side, a key intermediate of umeclidinium, on the other side to give the umeclidinium impurities more frequently detected.

Another purpose of the invention is to provide some reference standards to detect impurity traces recurring in the preparation of umeclidinium and a process for their preparation.

DESCRIPTION OF THE INVENTION

According to one of its aspects, object of the invention is a process for the preparation of a compound of formula (I) and its salts (I)

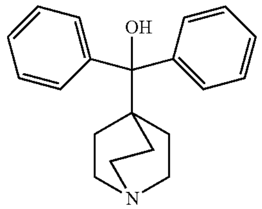

which comprises reacting a compound of formula (II)

(II)

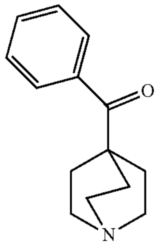

with a compound selected from phenyllithium and phenyl magnesium bromide, in a suitable solvent, optionally isolating the compound and optionally transforming it into one of its salts.

The reaction is preferably carried out in a solvent preferably selected among aprotic solvents, for example ethers, in particular tetrahydrofuran (THF) or methyl-tert-butyl ether (MTBE) or aliphatic or aromatic hydrocarbons, preferably toluene. Solvent mixtures can also be used.

According to a preferred embodiment, the reaction is carried out under inert atmosphere, for example under nitrogen atmosphere.

Phenyllithium is used in stoichiometric amount to the compound of formula (II) or, preferably in slight excess, for example 1.2-1.3 moles phenyllithium per mole compound of formula (II). Advantageously, phenyllithium is added drop-wise to the reaction mixture containing the compound of formula (II) and the solvent.

The reaction can be carried out at room temperature and is completed in very short time, in practice, at the end of the dripping, and the compound of formula (I) can be isolated according to the conventional techniques, for example by extraction.

The compound of formula (II) is a novel compound and is a further object of the invention, together with its salts. Such salts can be pharmaceutically acceptable or non-pharmaceutically acceptable; anyway the pharmaceutically acceptable salts are preferred.

The salts of the compound of formula (II) are preferably selected among hydrochloride, hydrobromide, sulphate, and phosphate. Anyway other salts can be prepared.

The compound of formula (II) can be prepared by reacting the compound of formula (III)

(III)

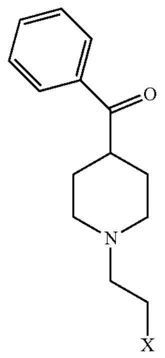

wherein X represents a leaving group, for example a halogen, tosyl, mesyl, triflate and the like, preferably a halogen and more preferably chlorine, in a suitable solvent, in the presence of a strong base.

As a strong base for example an alkaline metal hydride, for example sodium hydride, can be used. However, as opposed to the processes of the known art, it is not necessary to use bases such as LDA or LiHMDS, that have the drawbacks described above.

The solvent that can be used in the above described reaction is preferably selected among toluene, tetrahydrofuran, dimethylformamide, tert-butanol, more preferably dimethylformamide.

According to a preferred embodiment, the reaction is carried out under inert atmosphere, for example under nitrogen atmosphere.

The reaction mixture is preferably heated at 40-70° C., advantageously 45-55° C.

Its completion can be followed by the known methods, for example by using chromatographic techniques. The compound of formula (II) can then be isolated according to conventional techniques, for example by extraction.

Alternatively, according to another embodiment of the invention, the compound (II) is prepared starting from the Weinreb amide of quinuclidine, depicted hereinbelow. Said amide is reacted with phenyllithium, or else phenyl magnesium bromide, in one or more suitable solvents, for example in tetrahydrofuran, to give the compound (II), according to the following reaction scheme.

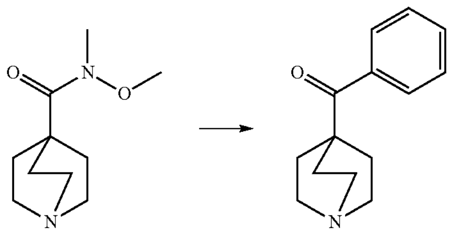

Weinreb Amide (II)

Some examples of the reactions of the invention are set forth in the Experimental Section of the present description.

Object of the invention is also a process for the preparation of the compound of formula (I) comprising:

reacting a compound of formula (III), as defined above, with a strong base in a suitable solvent, to give the compound of formula (II) and, subsequently reacting the compound of formula (II) with phenyllithium in a suitable solvent, to give the compound of formula (I).

Alternatively, object of the invention is also a process for the preparation of the compounds of formula (I) and (II)

reacting the Weinreb amide of quinuclidine with phenyllithium or phenyl magnesium bromide, thus obtaining the compound of formula (II) and optionally reacting the compound of formula (II) with phenyl lithium or phenyl magnesium bromide in a suitable solvent, to obtain the compound of formula (I).

The preferred and advantageous embodiments mentioned above apply also to the latter process.

The compound of formula (III) is known in the art and can be prepared for example as described in *Eur. J. Med. Chem.* (1997), 3:651-659 (therein described as compound 5).

The above mentioned Weinreb amide of quinuclidine is also itself known in the art and is described for example in WO99/21855.

According to another of its aspects, object of the invention is the use of the compound of formula (II) and the compound of formula (III) for the preparation of the compound of formula (I) and as synthesis intermediates, in particular but not only, of umeclidinium.

It is easily understood that the reaction of the invention for the preparation of the compound of formula (I) provides some advantages to the known art, as it allows using less phenyllithium and consequently obtaining less reaction by-products. Furthermore, the alpha hydrogen to the ketone in the compound of formula (II) is more activated than the corresponding hydrogen of the ethyl isonipecotate derivative used in the prior art and therefore the carbanion necessary for the reaction is more easily formed, and allows the use of conventional bases (such as alkaline hydrides), thus avoiding the need to use particular and problematic bases such as those previously cited.

Furthermore, with respect to what has been obtained with the prior art processes, the compound of formula (I) obtained according to the invention contains less reaction by-products, in particular less impurities of general formula (IV)

(IV)

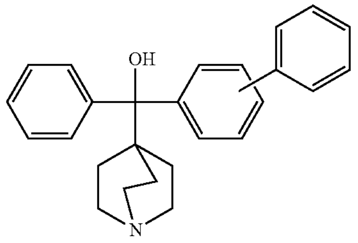

According to another of its aspects, object of the invention are the compounds of the general formula (IV) and in particular the compounds having the following formulas:

(V)

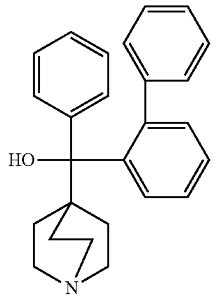

(VI)

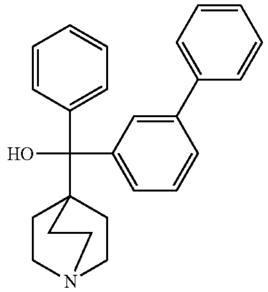

(VII)

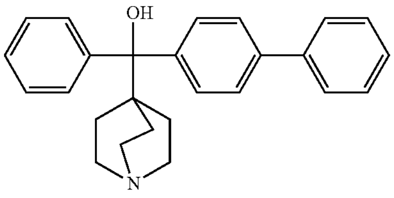

As it will be demonstrated in the Experimental Section, the compound of formula (I) and umeclidinium prepared according to the processes of the known art, contain many impurities. It is well know that, mainly in the pharmaceutical field, the presence of impurities must be as low as possible.

As it will be demonstrated in the following Experimental Section, the purity of the compound of formula (I), obtained by the compound of formula (II) object of the invention, has been compared to the purity of the same compound obtained according to known art (WO2005/104745) by using the same raw materials, and it can be observed that the compound obtained according to the present invention contains about half the impurities of the general formula (IV).

The presence of such impurities has been detected and quantified by UPLC-MS.

According to another of its aspects, object of the invention is the compound of formula (I) containing less than 2%, preferably less than 1.5%, for example about 1-1.3%, of one or more compounds of formula (IV).

According to another of its aspects, object of the invention is the use of the compound of formula (I) containing less than 2%, for example 0.5-2%, preferably less than 1.5%, for example about 1-1.3%, of one or more compounds of formula (IV), for the preparation of umeclidinium.

The compound of formula (I) can be transformed into the umeclidinium according to the methods known in the art, for example as described in WO2014/027045.

When the compound of formula (I) is converted into the umeclidinium, it transports with itself the impurities (compounds of formula (IV)) that are converted in the corresponding compounds of the general formula (VIII)

(VIII)

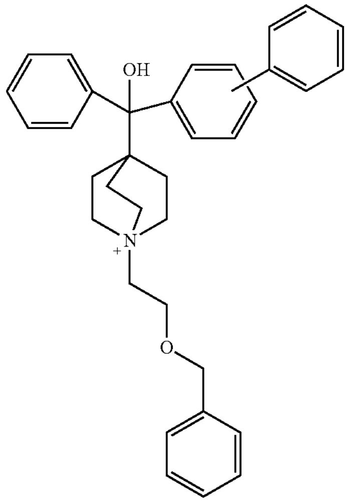

(IX)

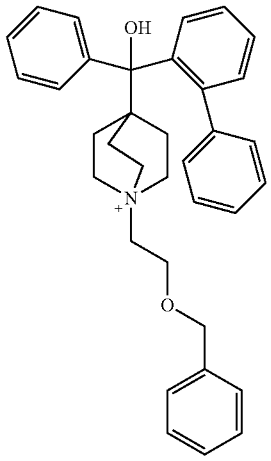

-continued (X)

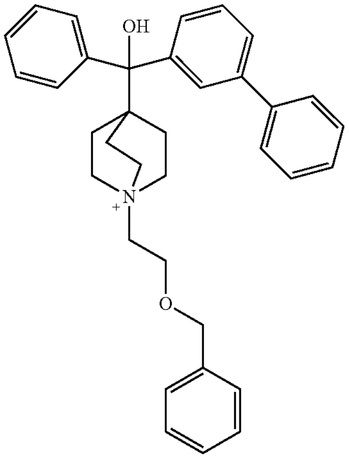

(XI)

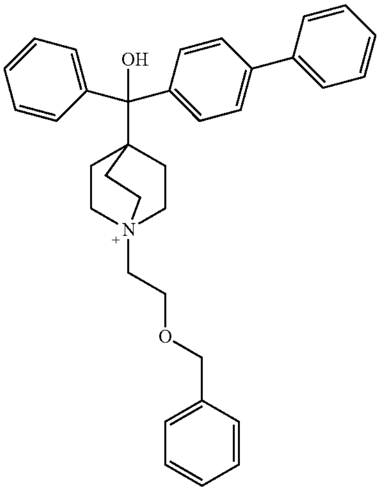

According to another of its aspects, object of the invention are the compounds of the general formula (IV) and (VIII), in particular the compounds (VI), (VI), (VII), (IX), (X) and (XI) and their use as reference standards to detect the presence and quantity of such impurities in the compound of formula (I), in the umeclidinium and in the pharmaceutical compositions containing it.

According to another of its aspects, object of the invention is a process for the preparation of a compound of formula (IV), in particular a compound of formula (V), (VI) and (VII), comprising reacting the compound (II) with biphenyllithium isomers, in a suitable solvent, for example tetrahydrofuran.

The compounds of formula (IX), (X) and (XI) can be prepared for example by quaternization of the compounds (V), (VI) and (VII) with ethyl benzyl ether bromide. Some of the examples of the processes of the invention are set forth in the following Experimental Section, by way of illustration only.

EXPERIMENTAL SECTION

Instruments

Figure 1:
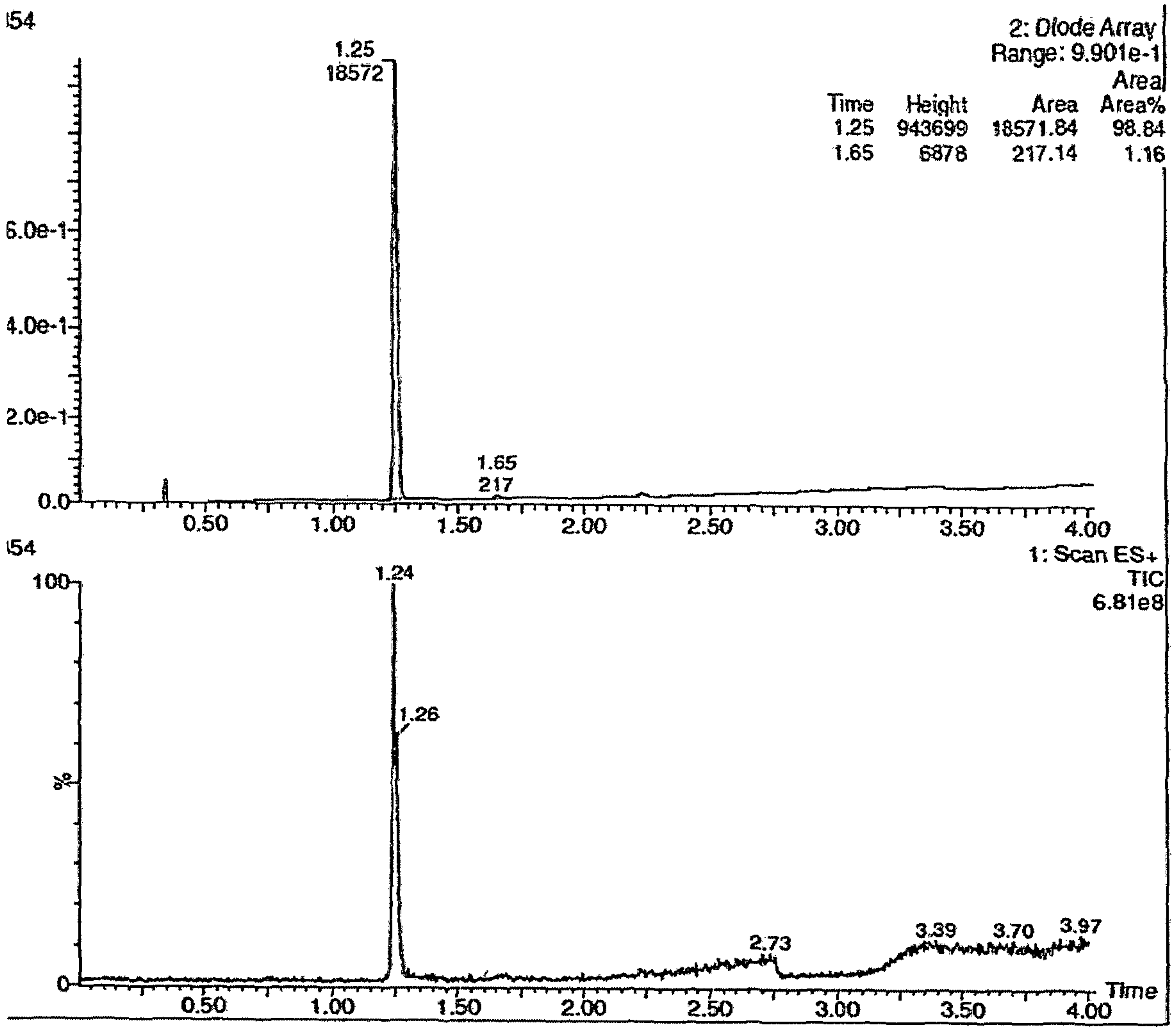
FIG. 1 shows UPLC-MS of diphenyl-quinuclidin-4-yl-methanol prepared starting from the compound of formula (II).

UPLC-MS: SWaters Acquity™ Ultra Performance Liquid Chromatography (UPLC).

Stationary phase: Acquity UPLC™ BEH SHIELD RP18, 1.7 um 2.1×50 mm.

Gradient: Acetonitrile with Water+TFA 5-100% in 4 min).

NMR: mBruker Avance 2, 300 MHz.

Example 1

Preparation of phenyl-quinuclidin-4-yl-methanone (Compound of Formula (II))

To a suspension of NaH (60% dispersion in mineral oil, 64.3 mg, 1.61 mmoles, 1.5 eq) in dimethylformamide (1 ml) under inert nitrogen atmosphere, a solution of phenyl-1-(2-chloroethyl)piperidin-4-yl-methanone (270 mg, 1.07 mmoles, 1 eq) in dimethylformamide (3 ml) is added. The reaction mass is heated to 50° C. until complete reaction, then $H_2O$ (3 ml) is dropped and is extracted with ethyl acetate (10 ml). The organic phase is dried on $Na_2SO_4$ and evaporated under vacuum, obtaining 148 mg title compound.

In order to fully characterize it, the product has been purified and Mass (FIG. 1) and NMR (FIG. 2) spectra were acquired.

$^1$H NMR (DMSO-$d_6$+TFA, 300 MHz): δ ppm: 9.55 (br s, 1H); 7.78-7.75 (m, 2H); 7.62-7.56 (m, 111); 7.53-7.48 (m, 21-1); 3.37-3.32 (m, 6H); 2.18-2.13 (m, 6H)

Example 2

Preparation of phenyl-quinuclidin-4-yl-methasone (Compound of Formula (II))

In a glass flask N-methoxy-N-methylquinuclidin-4-carboxyamide (828 mg, 84.12% by weight, 3.51 mmol, 1 eq) is loaded in THF (18 ml) and the solution is cooled to −20° C.

A solution of phenyllithium (1.9M in dibutyl ether, 6.27 mmol, 3.3 ml, 1.79 eq) is added dropwise. The reaction is quenched with water (1 ml) and concentrated under vacuum to eliminate THF. The residue is reworked with ethyl acetate and $Na_2CO_3$(aq) saturated solution. The organic phase is separated and the product is extracted again with ethyl acetate. The organic phases are put together, washed with a 1M NaOH solution, then anhydrified on sodium sulphate, filtered and concentrated under vacuum. After chromatographic purification, phenyl(quinuclidin-4-yl)methanone has been obtained as yellow oil (496 mg, 96.94% UPLC purity, 64% yield).

Mass and NMR confirm the structure:

UPLC MS: m/z 216.31 (MH+)

$^1$H NMR (DMSO-$d_6$, 300 MHz): δ ppm: 7.66-7.63 (m, 2H); 7.52-7.42 (m, 3H); 3.82-2.78 (t, 6H), 1.77-1.72 (t, 6H).

Note. δ ppm: 3.32 (s): $H_2O$; 2.51 (quint): DMSO

Example 3

Preparation of diphenyl-quinuclidin-4-yl-methanol (Compound of Formula (I))

To a solution of phenyl-quinuclidin-4-yl-methanone (28 mg, 0.130 mmoles, 1 eq) in 1.2 ml toluene and under nitrogen atmosphere, a solution of phenyllithium (1.9M in dibutylether, 0.082 ml, 0.156 mmoles, 1.2 eq) is dropped. $H_2O$ (1.5 ml) is added and is extracted with ethyl acetate (2×7 ml). The organic phases put together are dried on $Na_2SO_4$ and concentrated under vacuum up to half the volume, thus obtaining the precipitation of a solid that is filtered and dried. 25 mg title compound is obtained as white solid.

The product has been characterized by acquiring the Mass (FIG. 3) and NMR (FIG. 4) spectra.

$^1H$ NMR (DMSO-$d_6$, 300 MHz): δ ppm: 7.54-7.52 (m, 411); 7.29-7.24 (m, 4H); 7.19-7.14 (m, 2H); 5.37 (s, 1H); 2.70-2.65 (m, 6H); 1.64-1.59 (m, 6H).

By UPLC-MS it has been observed that the impurities of formula (IV) (sum of the compounds (V), (VI), (VII)) is lower than 1.5% in the obtained compound (FIG. 1). In said figure, at 1.65 minutes, a peak that integers 1.16% (in a lower percentage than what is obtained by the ester directly from the quinuclidine ethyl ester according to WO2005/104745 (see comparative example)) is obtained.

Comparative Example

Preparation of diphenyl-quinuclidin-4-yl-methanol According to the Known Art The title compound is prepared as described in WO2005/104745, by using the same batch of phenyllithium of Example 3 (therefore containing the same impurities).

Figure 2:
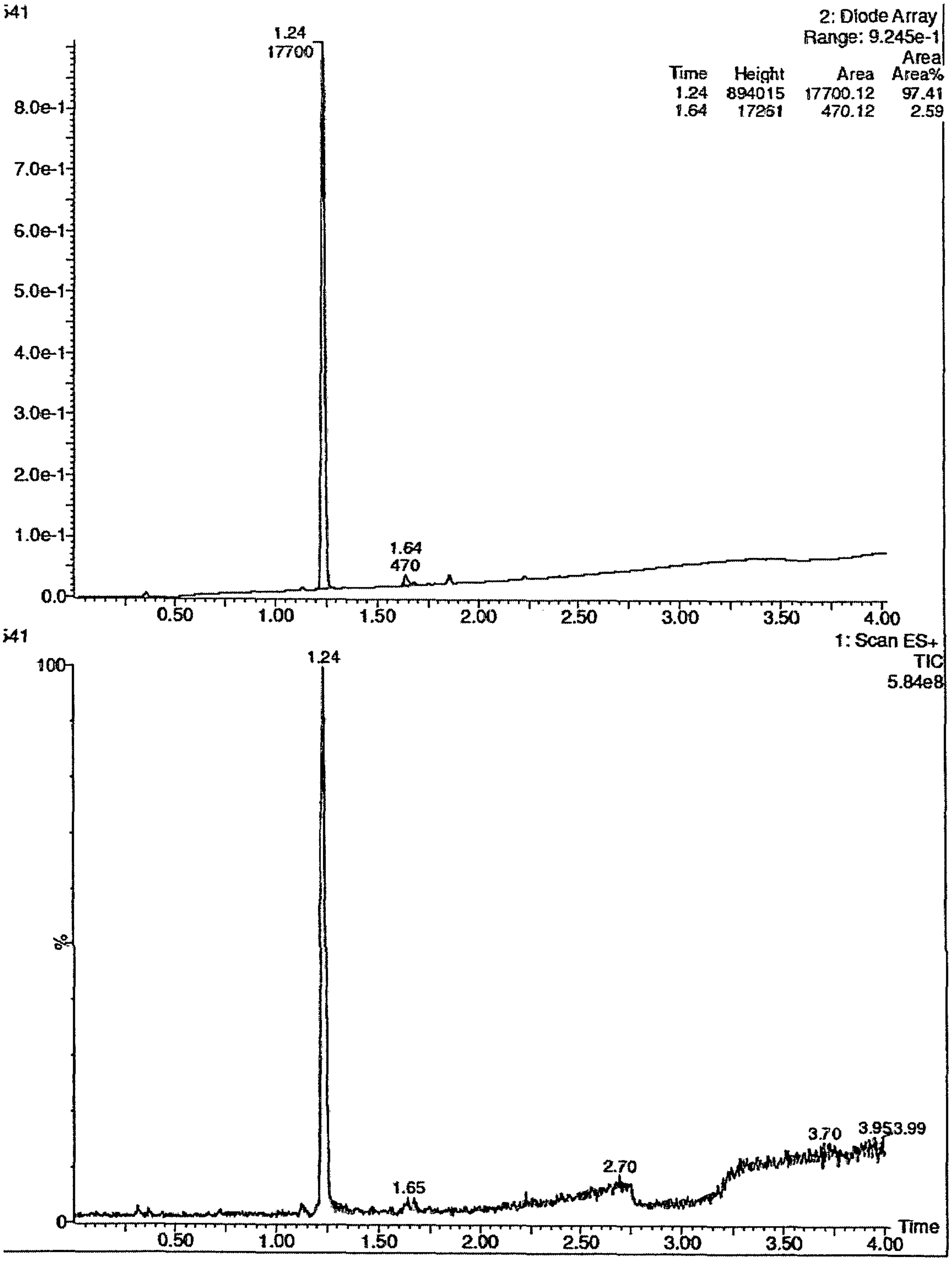
FIG. 2 shows UPLC-MS of diphenyl-quinuclidin-4-yl-methanol prepared according to the known art.

By UPLC-MS it has been observed that the impurities of formula (IV) are higher (as a sum) than 2.5% (FIG. 2).

Preparation of Standards (Impurities)

Example 4

Preparation of [1,1'-biphenyl]-2-yl(phenyl)(quinuclidin-4-yl)methanol (Compound of Formula (V))

2-bromobiphenyl (112.9 mg, 0.484 mmol, 1.90 eq) is dissolved in anhydrous THF (1.5 ml), the solution is cooled to −78° C. and n-butyllithium (1.6M in n-esane, 0.504 mmol, 0.315 ml, 1.98 eq) is added dropwise. After 7 minutes it is added dropwise to a solution of phenyl(quinuclidin-4-yl)methanone (55 mg, 0.255 mmol, 1 eq) in toluene (1.5 ml) at −26° C. The solution is quenched with water. A $Na_2CO_3$ (aq) saturated solution is added and it is extracted once with EtOAc. The organic phase is anhydrified on sodium sulphate and the solvent evaporated under vacuum, providing crude [1,1'-biphenyl]-2-yl(phenyl)(quinuelidin-4-yl)methanol. The product has been purified by chromatography to perform the NMR characterization. [1,1f-Biphenyl]-2-yl(phenyl)(quinuclidin-4-yl)methanol trifluoroacetate has been obtained as white solid (26.21 mg, 100% chromatographic purity, 21% yield)

Mass and NMR confirm the structure:

UPLC MS: m/z 370.31 (MH+)

$^1H$ NMR (DMSO-$d_6$+TFA, 300 MHz, 343K): δ ppm: 9.13 (br s, 1H); 8.02-7.99 (d, 1H); 7.40-7.35 (td, 1H); 7.30-7.25 (td, 1H); 7.15-6.90 (m, 10H), 6.52 (br m, 1H), 3.28-3.23 (t, 6H); 2.07-2.02 (t, 6H).

Note 1: δ ppm: 2.51 (quint): DMSO

Note 2: for reasons of resolution, TFA has been added in the NMR tube and, consequently, the OH proton is not visible.

Example 5

Preparation of [1,1'-biphenyl]-3-yl(phenyl)(quinuclidin-4-yl)methanol (Compound of Formula VI))

3-bromobiphenyl (37 mg, 0.159 mmol, 1.36 eq) is dissolved in anhydrous THE (0.9 ml), the solution is cooled to −78° C. and n-butyllithium (1.6M in n-esane, 0.160 mmol, 0.100 ml, 1.37 eq) is added dropwise. After 10 minutes it is added dropwise to a solution of phenyl(quinuclidin-4-yl)methanone (25.2 mg, 0.117 mmol, 1 eq) in toluene (0.7 ml) at −26° C. The solution is quenched with water (0.3 ml). A $Na_2CO_3$(aq) saturated solution is added and it is extracted 2 times with EtOAc. The organic phases are put together, are anhydrified on sodium sulphate and the solvent is evaporated under vacuum, providing [1,1'-biphenyl]-3-yl(phenyl)(quinuclidin-4-yl)methanol. The product has been purified by chromatography to perform the NMR characterization. [1,1'-Biphenyl]-3-yl(phenyl)(quinuclidin-4-yl)methanol trifluoroacetate has been obtained as white solid (24.3 mg, 99.7% chromatographic purity, 43% yield)

Mass and NMR confirm the structure:

UPLC MS: m/z 370.31 (MH+)

$^1H$ NMR (DMSO-$d_6$, 300 MHz): δ ppm: 9.21 (s, 1H); 7.74 (s, 1H); 7.64-7.23 (m, 13H); 6.03 (s, 1H), 3.26-3.21 (br t, 6H); 2.02-1.97 (br t, 6H).

Note: δ ppm: 2.51 (quint): DMSO, with satellite peaks

Example 6

Preparation of [1,1'-biphenyl]-4-yl(phenyl)(quinuclidin-4-yl)methanol (Compound of Formula (VII))

4-bromobiphenyl (482 mg, 2.07 mmol, 1.07 eq) is dissolved in anhydrous THF (5 ml), the solution is cooled to −78° C. and n-butyllithium (1.6M in n-esane, 2.08 mmol, 1.3 ml, 1.08 eq) is added dropwise. After 5 minutes it is added dropwise to a solution of phenyl(quinuclidin-4-yl)methanone (416 mg, 1.93 mmol, 1 eq) in toluene (7 ml) at −26° C. The solution is quenched with water (1 ml). A $Na_2CO_3$(aq) (20 ml) saturated solution is added and it is extracted with EtOAc (2×40 ml). The organic phases are put together, are anhydrified on sodium sulphate and the solvent is evaporated under vacuum, providing [1,1'-biphenyl]-4-yl(phenyl)(quinuclidin-4-yl)methanol as white solid (816 mg, 77.5% chromatographic purity, 88.6% yield).

A portion has been purified by chromatography to perform the NMR characterization:

Mass and NMR confirm the structure:

UPLC MS: m/z 370.28 (MH+)

$^1H$ NMR (DMSO-$d_6$, 300 MHz): δ ppm: 9.17 (s, 1H); 7.67-7.58 (m, 8H); 7.49-7.44 (t, 2H); 7.39-7.32 (m, 3H), 7.28-7.23 (m, 1H); 5.97 (s, 1H); 3.24 (br t, 6H), 2.01-1.96 (br t, 6H).

Note: δ ppm: 3.46 (s): $H_2O$; 2.51 (quint): DMSO, with satellite peaks.

Example 7

Preparation of 4-([1,1'-biphenyl]-2-yl(hydroxy)(phenyl)methyl)-1-(2-(benzyloxy)ethyl)quinuclidin-1-io bromide (Compound of Formula (IX))

[1,1'-biphenyl]-2-yl(phenyl)(quinuclidin-4-yl)methanol (3.08 mg, 0.00834 mmol, 1 eq) is suspended in acetone (0.6 ml), ((2-bromoethoxy)methyl)benzene (2.5 mg, 0.0116 mmol, 1.39 eq) is added and it is refluxed for 11 hours. It is cooled to room temperature, the mixture is centrifuged, the supernatant is removed and the operation is repeated by washing the white solid with acetone. 4-([1,1'-Biphenyl]-2-yl(hydroxy)(phenyl)methyl)-1-(2-(benzyloxy)ethyl)quinuclidin-1-io bromide is obtained (1.6 mg, 98.35% chromatographic purity, 32% yield). By concentrating the supernatant it is possible to precipitate additional 5.3 mg product, having 71% purity).

Mass and NMR confirm the structure:

UPLC MS: m/z 504.50 (M+)

$^1$H NMR (DMSO-$d_6$, 300 MHz, 342K): δ ppm: 8.01-7.98 (d, 1H); 7.42-6.91 (m, 17H); 6.53 (br s, 1H); 4.87 (s, 1H); 4.53 (s, 2H); 3.87-3.84 (t, 2H); 3.53-3.48 (t, 6H); 3.40-3.37 (t, 2H); 2.15-2.10 (br t, 6H)

Note: δ ppm: 3.10 (s): $H_2O$; 2.51 (quint): DMSO

Example 8

Preparation of 4-([1,1'-biphenyl]-3-yl(hydroxy)(phenyl)methyl)-1-(2-(benzyloxy)ethyl)quinuclidin-1-io bromide (Compound of Formula (X))

[1,1'-biphenyl]-3-yl(phenyl)(quinuclidin-4-yl)methanol (14.13 mg, 0.0382 mmol, 1 eq) is solubilized in acetone (1 ml), ((2-bromoethoxy)methyl)benzene (11 mg, 0.0511 mmol, 1.34 eq) is added and it is refluxed for 11 hours. It is cooled to room temperature, diethyl ether is added, it is concentrated under vacuum to a small volume and filtered by washing the solid with the minimum amount of a 6/1 diethyl ether/acetone mixture. 4-([1,1'-biphenyl]-3-yl(hydroxy)(phenyl)methyl)-1-(2-(benzyloxy)ethyl)quinuclidin-1-io bromide is obtained (20 mg, 90% chromatographic purity, 80% yield).

Mass and NMR confirm the structure:

UPLC MS: m/z 504.57 (M+)

$^1$H NMR (DMSO-$d_6$, 300 MHz): δ ppm: 7.74 (br t, 1H); 7.65-7.23 (m, 18H); 6.07 (s, 1H); 4.50 (s, 2H); 3.82 (br t, 2H); 3.51-3.46 (t, 6H); 3.37 (br t, 2H); 2.08-2.03 (br t, 6H).

Note: δ ppm: 3.32 (s): $H_2O$; 2.51 (quint): DMSO, with satellite peaks; 2.09 (s): acetone Example 9

Preparation of 4-([1,1'-biphenyl]-4-yl(hydroxy)(phenyl)methyl)-1-(2-(benzyloxy)ethyl)quinuclidin-1-io bromide (Compound of Formula (XI))

[1,1'-biphenyl]-4-yl(phenyl)(quinuclidin-4-yl)methanol (6.74 mg, 0.0182 mmol, 1 eq) is suspended in acetone (0.5 ml), ((2-bromoethoxy)methyl)benzene (4.7 mg, 0.0219 mmol, 1.2 eq) is added and it is refluxed for 11 hours. The solution is concentrated under vacuum to a small volume and the product is filtered, by washing it with the minimum amount of acetone. 4-([1,1'-Biphenyl]-4-yl(hydroxy)(phenyl)methyl)-1-(2-(benzyloxy)ethyl)quinuclidin-1-io bromide is obtained (9.91 mg, 93% chromatographic purity, 87% yield).

Mass and NMR confirm the structure:

UPLC MS: m/z 504.50 (M+)

$^1$H NMR (DMSO-$d_6$, 300 MHz): δ ppm: 7.67-7.59 (m, 8H); 7.49-7.44 (t, 2H); 7.39-7.24 (m, 9H); 6.01 (s, 1H); 4.50 (s, 2H); 3.83 (br t, 2H); 3.51-3.47 (br t, 6H); 3.38 (br t, 2H); 2.07-2.02 (br t, 6H)

Note: δ ppm: 3.32 (s): $H_2O$; 2.51 (quint): DMSO, with satellite peaks

The invention claimed is:

1. A Process for the preparation of a compound of formula (I) or one of its salts (I)

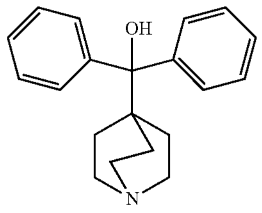

which comprises reacting a compound of formula (II)

(II)

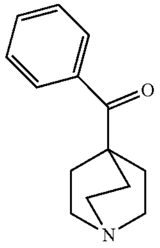

with a compound selected from phenyl lithium and phenyl magnesium bromide, in a suitable solvent, optionally isolating the so-obtained compound of formula (I) and optionally transforming it into one of its salts.

2. The process according to claim 1, wherein said solvent is selected from aprotic solvents.

3. The process according to claim 1, wherein phenyl lithium is used at a rate of 1.2-1.3 moles per mole of compound of formula (II).

4. The process according to claim 1, wherein said compound of formula (II) is obtained by reacting a compound of formula (III)

(III)

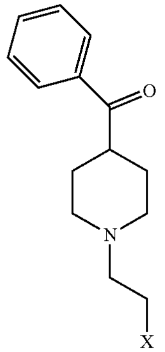

wherein X is a leaving group with a strong base in a suitable solvent, to give the compound of formula II (II)

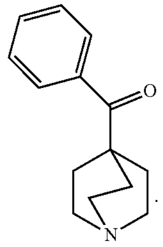

.

5. The process according to claim 1, wherein said compound of formula (II) is obtained by reacting the Weinreb amide of quinuclidine with phenyl lithium or phenyl magnesium bromide.

6. The process according to claim 1, wherein said solvent is selected from aprotic solvents and mixtures thereof.

7. The process according to claim 1, wherein said solvent is selected from the group consisting of ethers, aliphatic hydrocarbons, aromatic hydrocarbons and mixtures thereof.

8. The process according to claim 1, wherein said solvent is selected from the group consisting of tetrahydrofuran (THF), methyl-tert-butyl ether (MTBE), toluene and mixtures thereof.

9. The process according to claim 1, comprising reacting said compound of formula (II) with phenyl lithium.

10. The process according to claim 1, wherein said phenyl lithium is added in stoichiometric amount or in slight excess with respect to the compound of formula (II).

11. The process according to claim 4, wherein said leaving group is selected from halogen, tosyl, mesyl and triflate.

12. A method of preparing the compound of formula (I) and/or umeclidinium using the compound of formula (II) and/or the compound of Formula (III) as intermediates (I)

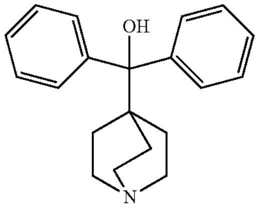

.

13. A compound of formula (II)

(II)

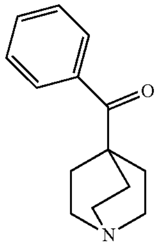

or one of its salts.

14. The salt of the compound of formula II (II)

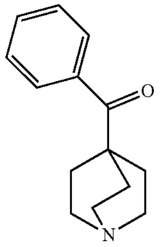

according to claim 13, wherein the salt is selected from the group consisting of hydrochloride, hydrobromide, sulphate and phosphate.

* * * * *